United States Patent [19]
Spranza, III

[11] Patent Number: 5,954,638
[45] Date of Patent: Sep. 21, 1999

[54] SURGICAL HARDWARE FOR HOLDING LIVE TISSUE

[76] Inventor: Joseph John Spranza, III, 12493 Old Rough & Ready Hwy., Grass Valley, Calif. 95945

[21] Appl. No.: 08/118,810

[22] Filed: Sep. 10, 1993

[51] Int. Cl.⁶ .................................................. A61B 17/02
[52] U.S. Cl. ............................................................ 600/201
[58] Field of Search ................................ 128/20, 17, 3; 606/191, 198; 604/104; 600/201, 206, 207, 208, 209

[56] References Cited

U.S. PATENT DOCUMENTS

| | | | |
|---|---|---|---|
| 3,515,129 | 6/1970 | Truhan | 128/20 |
| 3,858,578 | 1/1975 | Milo | 128/20 |
| 4,984,564 | 1/1991 | Yuen | 128/20 |
| 5,159,921 | 11/1992 | Hoover | 128/20 |
| 5,284,130 | 2/1994 | Ratliff | 128/20 |

FOREIGN PATENT DOCUMENTS

| | | | |
|---|---|---|---|
| 736480 | 6/1943 | Germany | 128/20 |
| 3813838 | 5/1989 | Germany | 128/20 |
| 938967 | 7/1982 | U.S.S.R. | 128/20 |
| 1489731 | 6/1989 | U.S.S.R. | 128/20 |
| 1563682 | 5/1990 | U.S.S.R. | 128/20 |

*Primary Examiner*—Joe Cheng

[57] ABSTRACT

A hand formable rod, band or sheet, consisting of a plurality of elements which are linked together in such a way that the whole can be either very flexible, or semi-rigid, or rigid. In the band, the elements have six degrees of freedom, providing unusual flexibility. This fabrication may be hand formed to a desired shape and then rigidified to a substantial stiffness. In the rigid state, this fabrication is strong enough to retract living tissue, and to perform as a mold, template, or fixator. The rigidity may be varied in very small increments by using a screw or screws acting upon tensioning cables. Tension causes increased friction between sliding surfaces. This friction creates stiffness and strength. Bending the fabrication does not cause material fatigue.

9 Claims, 7 Drawing Sheets

SURGICAL HARDWARE FOR HOLDING LIVE TISSUE

BACKGROUND—FIELD OF INVENTION

This invention relates to surgical instrumentation used for retracting parts of the patient's body during surgery, which instrumentation provides the surgical team greater access, greater visibility and reduced manpower requirements during the procedure.

BACKGROUND—DESCRIPTION OF PRIOR ART

In surgery, it is frequently necessary to spread apart the walls of the incision to enable the surgical team to obtain physical and visual access to the object of the procedure. Historically, this retraction was accomplished with one or more specially pre-shaped grapplers, (often called "spoons" and "blades"), the bulk of which were either manually or mechanically held outside the incision, across the patient, and the ends of which were intruded into the incision, pulling against the walls of the tissue, thereby spreading it to expose the appropriate area of the surgery. One such grappler is a "Homan" retractor, which resembles a shoehorn with a heavy long handle and a 90 degree bend between the "spoon" and this handle. Another is a "Cobra" which is similar to the "Homan" but with a tooth at the end of the spoon portion, to allow digging in and levering, much as with a pike. It will be appreciated that at least two such retractors are required to afford reasonable spreading, and in many cases more than two are required. In hip arthroplasties, it is not uncommon to employ 5 retractors simultaneously, when counting "self retaining" retractors. As the required depth of surgery increases, the strength of the retractors must be increased to compensate for the added beam stress, and so, therefore, the bulk of the retractors increases, reducing accessibility to the object of the surgery. Keeping the incision as small as practical is a priority. It will be readily apparent that as the retractors become larger and greater in number, they collectively take up more volume and the remaining space becomes smaller, affording less access for the surgical team. Another consideration is fatigue. Since modern surgeries are very complex and require hours to complete, it is commonplace to require tension on the retractors for an hour or more at a time. It is imperative that the surgeon have a good line of sight, and a clear path for the surgical lights to illuminate the surgery. This requires highly specific shaping of the tissue. Understandably, it is quite tiring and boring for the people providing this holding service, and many times during a procedure the chief surgeon must ask for a retractor to be pulled tighter or to be pulled in the original direction, the assistant having relaxed or moved. Further, it is not uncommon to have two persons each holding retractor handles, and these additional "bodies" impede the motion of the chief surgeon. As surgeries become more complex, larger surgical teams are required, mandating the elimination of any personnel not absolutely required. Dollar costs are also critical. Every person is expensive. Cutting the required number of operating room personnel results in a direct monetary savings. There is simply not space enough nor money enough for more "bodies" and therefore any reduction in manpower is highly desirable. The need for new and improved retractors is very real and very critical. Many solutions have been proposed, in an effort to reduce the number of hands, to reduce the amount of hardware, to increase the accessibility to the object of the surgery, to provide a clear line of sight, to enhance illumination, to save time, to save money.

To reduce the number of "hands" required to hold retractors, a number of devices have been introduced in the last thirty years. The "Charnley retractor" is a tubular metal three sided frame which lies on top of the patient, and to which the grapplers are fastened. This frame does take the place of a hand, maybe even two, but there are some shortcomings. Such frames all too frequently slide around and even slip off the patient at inconvenient times, resulting in confusion and loss of focus for the team. Eftekhar showed a ring retractor in the first quarter of the 1980's which is a modified vaginal retractor. This instrumentation was modified for use in total hip surgery. The Eftekhar modified vaginal retractor was named the "Octomerius" and used much the same principles as the Charnley retractor, but was smaller and utilized multi-lead screws for quick action in pulling on the grapplers. This Octomerius retractor rests atop the patient, as does the Charnley. There is no patent issued on the Eftekhar modified vaginal retractor. There is a patent on an expanding retractor, Deutsches Reich patent number 736 480 by Schwab. This patent shows a uniformly expanding multi-link scissors type retractor. The Schwab device provides only uniformly variable circular retraction, and only on one plane. Evidently, "Schwab" does not satisfy the requirement for highly specific shaping.

Other devices have been introduced which provide a mechanical means of holding the grapplers to posts fastened to the surgical table. One such retractor is the subject of patent number 5000163, (issued to Ray in 1991). A second of this type of retractor is disclosed in patent number 3858578 by Milo. It describes a post in the form of a flexible arm, one end of which fastens to the surgical table frame. The other end is a connector with a female threaded hole onto which a retractor may be fastened by a screw. Mechanically, this arm consists of a multiple of cylindrical "dovetail" elements which fit head into tail, one into the other, into the next, and so on. The whole group of these elements is fastened together more or less tightly by a cable. This cable is tensioned by fluid force acting upon a piston in the end of the arm which fastens to the table frame. Apparently, this device is not commercially available. One reason for the lack of popularity of the Milo arm is surely that it is not directionally uniformly stiff. That is, the force required to curve the arm is much greater than the force required to un-curve the arm. This force difference results from the significant change of length of the cable when the arm is curved as compared to when the arm is straight. This force difference means that the arm has an unacceptable difference in strength, as a function of the force vector. Such a difference is a serious shortcoming in a shapeable retractor. A further drawback to the Milo arm is the need to provide an external power source such as a foot pump, and a valve to control the power. Such accessories clutter the floor and the cords and tubes running up and over the surgical table interfere with free movement around the surgical sight and disturb the sterile draping on the operating table. In patent number 5284130 issued in 1994 to Ratliff, an arm (or several arms) is shown which is very close to the Milo arm. Ratliff shows an arm made up of a number of elements which seem to fit together (in the way of a concave and convex surface) and which are "compressed" together (to cause frictional rigidity) by a cable acted upon by a piston. The piston is acted upon by a fluid, such as gas pressure which is obtained from an outside source. The differences between Milo and Ratliff are difficult to perceive, but both appear to suffer from the same drawbacks, they both are subject to variations in stiffness as a function of direction, they are both large, and they both require an external power source. But, they are only arms which fasten to the sides of the table frame. In a patent (number 938967) of the Neurosurgery Institute of the Soviet Union (NEUR) in 1982, another arm, (again like Milo) is shown. This arm is described as a "multi-link hose" to be used for holding surgical instruments. One end of the "hose" is a clamp which is like a table frame clamp and the other end is a vice-like clamp which is capable of holding a surgical instrument. This "hose" has elements which fit together as a ball and socket and are compressed more or less tightly by a cable. The cable is tensioned by a screw and wing nut, instead of a piston and external power source. In fact, the NEUR hose is another arm, like Milo and Ratliff, which fastens to the surgical table frame. Each of the inventions, Ray, Milo, Ratliff and NEUR are amongst that hardware which fastens to the table and telescopes out onto or over the surgical subject. It is worth noting that such post and arm devices are widely viewed as cumbersome, tedious to attach, slow to adjust, and that they interfere with the sterile draping. Further negatively, the posts are often in the way of the surgical team. These devices are labor intensive to clean and sterilize.

Another type of retractor, one example of which is described by patent number 4889107, (issued 1989 to Kaufman), is a solid malleable rod or bar or sheet, often of metal such as aluminum or stainless steel, which the surgeon can fashion into a shape suitable for holding apart the walls of the incision. In some cases these malleable bars are encased in a plastic barrier sheet or mesh, in an attempt to enhance their compliance and their grip. A second example of this type of retractor is shown in patent number 4789195, (issued 1989 to Seare). Therein is described a flat sheet of metallic lead cut to the silhouette of a person's hand which lead sheet may be bent to a shape suitable for holding a human hand during hand surgery. One limitation of these devices is that they do not offer enough degrees of freedom, and therefore are not readily shaped into a form suitable for three dimensional space. That is, these devices do not provide highly specific shaping of tissue. This will be easily appreciated if you attempt to form a venetian blind slat (or a belt) into a cone having a planar base. The base of the cone has a larger radius, hence a longer periphery than the top of the cone. And, since you can not readily stretch and shrink materials, you will be unable to obtain a satisfactory shape by your hands. The result will always have a "V" shaped base. Truhan, in patent number 3515129 presents a specification for a band which is cut at regular intervals, the incision running from each outer edge toward the center. This cutting partially relieves the inherent rigidity about the width of the band, but not enough to allow the band to be usefully flexible for surgery. Also, in Truhan the elements are not capable of being moved in a number of degrees of freedom. The Truhan elements are an integral part of the plastic band from which they are partially fretted. It is not possible, for example, to rotate an element about the linear axis of the plastic band, relative to the adjacent elements. Nor, in Truhan, can the elements be rotated about an axis which is perpendicular to the linear axis. In other words, the Truhan device does not allow highly specific shaping of tissue. An additional problem is that fatigue fractures occur when a material is repeatedly bent and straightened. Fatigue fractures lead to failure of the retractor. Failure of the retractor leads to extended surgery time with increased expense and a frustrated surgeon, in the best case.

Another type of retractor is the inflatable or evacuatable tube or cuff. One example of this type of retractor is shown in patent number 4984564 by Yuen. Herein is described an inflatable sleeve which has a tightly rolled shape, (such as a roll of paper) when relaxed, but when inflated opens out into a larger circle. This device is not commercially in evidence, at least not as patented, perhaps due to the fact that it is necessarily large and therefore obstructs the surgical area. Additionally, if made as shown in the specification, this rubber cuff would coil in, not coil out, due to the juxtaposition of the cells to the "belt." In any event, the device would not have any significant strength unless it was entirely too thick in section to be of use around a human body and further, unless the inflation pressures were dangerously high. The lack of strength is due to the elasticity of the material and the limited fluid pressure which can safely be contained therein. Additionally, the Yuen device may not be shaped and then rigidified to hold that shape; it does not provide highly specific shaping. It is only capable of exerting limited force outward, or inward as an inflatable cuff. Finally, the Yuen device requires an external pressure source. Hoover shows in patent number 5159921, a circular plastic ring, the interior section of which is filled with elastic beads. As the bead filled section is evacuated, the plastic ring is reported to become rigid. Hoover's device is, as all of the others above, limited as to flexibility and stiffness. Also, the Hoover device is not sectional, and would tend to obstruct surgical procedures. The Hoover invention is apparently not commercially available. Pallin, in patent number DE 3813-838-A describes a "flat, insulated and flexible base" onto which is applied a number of square electrodes. The abstract drawing shows this sheet rolled up on opposite ends. Of course, being a flat sheet it may only be rolled about a single axis, (and therefore not capable of assuming a spherical section) and it is not intended to be rigidified.

It is one purpose of this invention to eliminate, to as great an extent as possible, the need for people to hold retractors. No one is required to hold this retractor once it is inserted. By eliminating this form of drudgery, one also cuts costs, and cuts impediments to access and visibility. Another purpose of this invention is to increase accuracy by increasing visibility. By providing a non-varying formable retractor which the surgeon can employ to quickly and easily shape the surgical opening to any highly specific shape required, this invention allows the surgeon to create a non-obstructed view and access to his goal. This invention eliminates obstructive hardware. The retractor of this invention may be shaped in a multiple of dimensions. No other retractor has ever offered so many degrees of freedom with elements which are shaped to grasp tissue. No other retractor has ever offered such complete element interlocking, allowing the surgeon such a wide variation in shape and size. Another purpose of this invention is to reduce surgical time by providing a non-varying retraction which may be set up quickly, but whenever required, changed quickly and easily. This invention provides a device which is partially or entirely inserted into the incision by the surgeon, and therein easily and quickly shaped and rigidified. The forces to shape or unshape the hardware of this invention are quite equal. Many previous retractors are stronger in one direction than in another. The retractor of this invention has essentially the same strength when forced in opposite directions. This equality of force results in a very stable retractor. This retractor remains where and how it is placed by the surgeon, until he wishes to modify it. This retractor moves with the patient. At such time as the surgeon wishes, repositioning and reshaping this retractor is simple and quick. No posts and other frames are required for this invention. This retractor requires no accessory equipment, such as air tanks, air lines, foot pumps, valves, electricity, or what have you to provide rigidity. It is self contained. This absence of wires, tubes, and chains allows more clear room in which to perform surgery. This retractor is easier to clean and sterilize than hardware which requires outside support equipment.

This invention is a fabric in the form of a rod, band or sheet, consisting of a plurality of elements which are tied together (linked) in such a way that the whole can be either very flexible, or semi-rigid, or rigid. The band is flexible with each element having six degrees of freedom. An analogous example of the flexibility of the band may be seen in a flexible cord, on which there are geometric elements which can be independently rotated with respect to the axis of the cord. Such elements on a flexible cord enjoy six degrees of freedom. In the sheet, the elements have less freedom, as in chain mail, but the sheet is flexible enough to be formed into sections of a sphere, and then rigidified. The strength of this rod, band or sheet is infinitely variable between the extremes of flexible and rigid, as a function of the tension. The rigidity is controlled by the degree of tension in the linking mechanism. When the tension is zero in the tensioning mechanisms of the band the elements are adequately free in all dimensions and the assembly is very limp. In this state, washing and sterilizing is easy because all surfaces are open to fluids. Pre-tensioning results in a hand formable band which retains the shape which you give it. Heavy tension causes the band to be stiff. Repeated bending and straightening of the rod or band or sheet does not lead to fatigue failure, as results from repeatedly bending and straightening solid materials. Relative motion of the elements is in fact obtained by sliding within the fabric mechanism. In this invention there is no fatigue failure because there is no actual bending of solid material, only sliding between the interfaces of the elements. The band can be readily hand shaped to the desired form while down in the incision. Further, the band can be formed into a helix or a cone, or practically any shape which is required. Cone shapes are important, due to the fact that the diameter at the top of a truncated cone is smaller than the base diameter. This smaller diameter can be made just large enough to see through and large enough to pass instruments, while the base diameter, being larger, would be large enough to expose underlying tissue for surgery. Such a cone allows greater access to the object of the surgery below, without requiring incising the overlying tissues to such a great extent. In surgery, it is often desirable to have a cone with a flat base. The hardware of this invention provides the option of shaping and holding a cone with a flat base. Other devices, when shaped into a cone, have a "V" or "U" shaped base. The retractor described here-in can be fashioned into a hoop of any of a range of desired diameters by simply overlapping the band upon itself and inserting one or both of the cross link pins (#10) which protrude from the tensioner cover (#9) into one or two holes in any element on the band. At least one set of cross link pins protrudes from the cover plate in the tensioner element. These cross link pins are fashioned to fit into the holes in any other element, in either the "Y" or "X" axis. If sections of the band overlap, these sections can be interlocked with the cross link pins in the tensioner cover, or other pins as required. Additionally, this invention serves to enshroud objects. While it can be inserted into and used to shape tissue, this invention is also very useful as an external collar, mold, or belt. Finally, when the retractor described here-in is of a satisfactory length and shape, a simple turn of a knob causes rigidification of the assembly, making it strong enough to hold open the incision. Additionally, the individual elements may be devised in a number of configurations. In FIG. 2 the elements are configured such that flesh conforms into and around them, causing a natural flesh retaining action, without trauma.

OBJECTS AND ADVANTAGES

Accordingly, several objects and advantages of this invention are as follows. This hardware may be used as a continuous band or sheet inside the incision, holding open the entire incision; a single retractor doing the job of several. Prior retractors are discrete, and a number must be used for adequate retraction. When used as a totally internal device, this retractor does not protrude above the surgical area unless the surgeon wishes a portion to be up and out of the incision. Prior retractors must protrude inconveniently above the incision, obstructing other instruments. This retractor does not require a person to hold it. This retractor allows hands free surgery; once installed it holds open the entire surgery site until the surgeon wishes to reshape it or remove it. This retractor will serve to hold other instruments, such as a suction tube, within accessory holes and within notches which are designed into the elements. This retractor may be used as a hand formable band, in which case a portion of the band may be utilized outside the incision as an anchor or loop. As a formable band or sheet, this retractor may be shaped in small areas to afford clear line of sight, or obstruction free access for surgical instruments. Because the elements of the band have six degrees of freedom, it is possible to shape this retraction system in ways and with a finesse unobtainable by any prior instrument. This retractor retains the shape given it by the surgeon. It has no hysteresis which solid metal displays when bent. But, this retractor also does not have fatigue failure as does solid material when repeatedly bent and straightened. This hardware may be used as a "curve tracer" in instances where the user wishes to copy a shape from one area and compare it to another area. This hardware may be used as a fixator, such that it can be formed around or along side an organ, and when shaped and rigidified, act as a "mandrel" to that organ. This retractor does not require external frames, rods, posts, chains, or what have you. Prior "hands free" retractors require a plethora of hardware to hold them over the incision. Such a plethora of hardware gets in the way of other surgical instruments. Further objects and advantages of this invention will become apparent from a consideration of the drawings and ensuing description of it.

DRAWING FIGURES

In the drawings, closely related figures have the same number but different alphabetic suffices.

Figure 1:
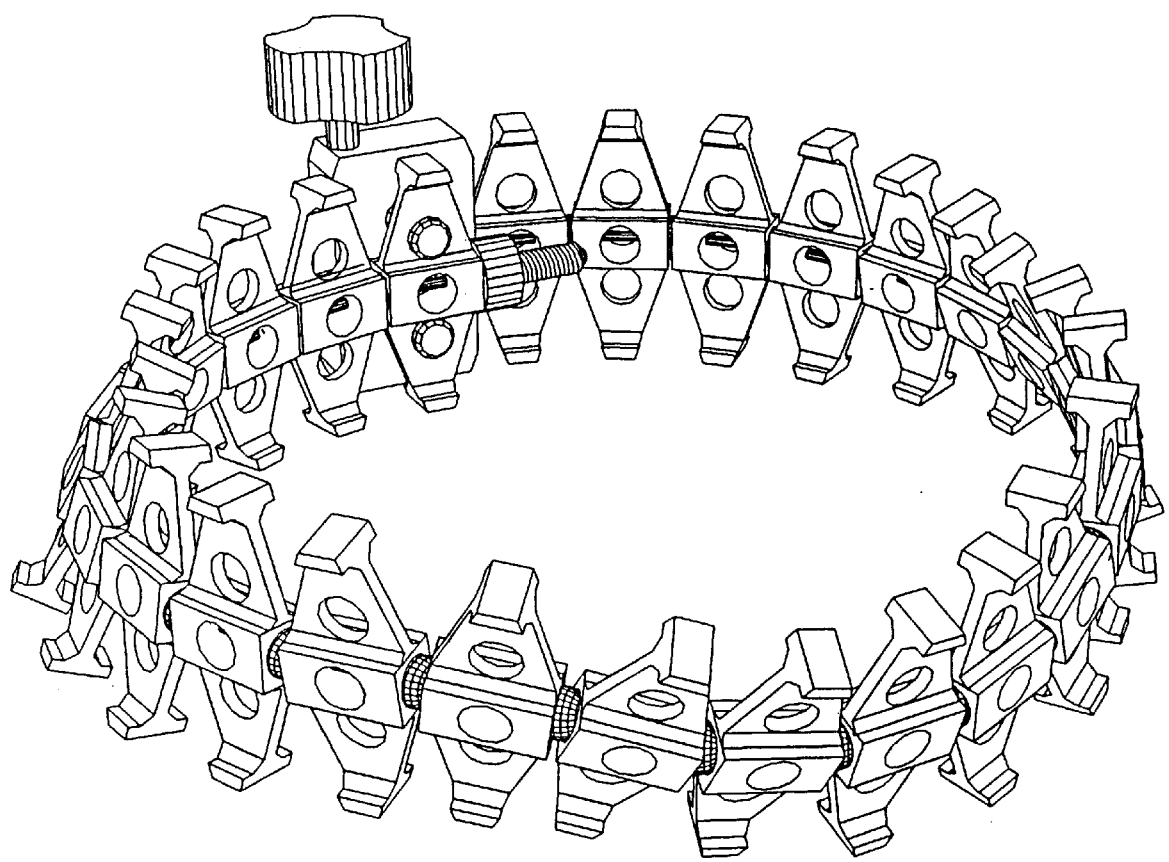
FIG. 1 shows an isometric view of a complete flexible band retractor.

| Reference Numerals In Drawings | |
|---|---|
| 1 element | 11 pre-tensioner screw |
| 2 transverse hole | 12 pre-tensioner knob |
| 3 spherical section seat | 13 accessory holes |
| 4 ball | 14 truncated angular section |
| 5 tension cable | 15 disk |
| 6 lever | 16 hole with locking bi-angle |
| 7 screw | 17 tensioner housing |
| 8 knob | 18 pre-tensioner element |
| 9 cover plate | 19 disk and ball loaded cable matrix |
| 10 cross link pins | 20 grooves across face |

DESCRIPTION—FIGS. 1 THROUGH 7

Figure 2:
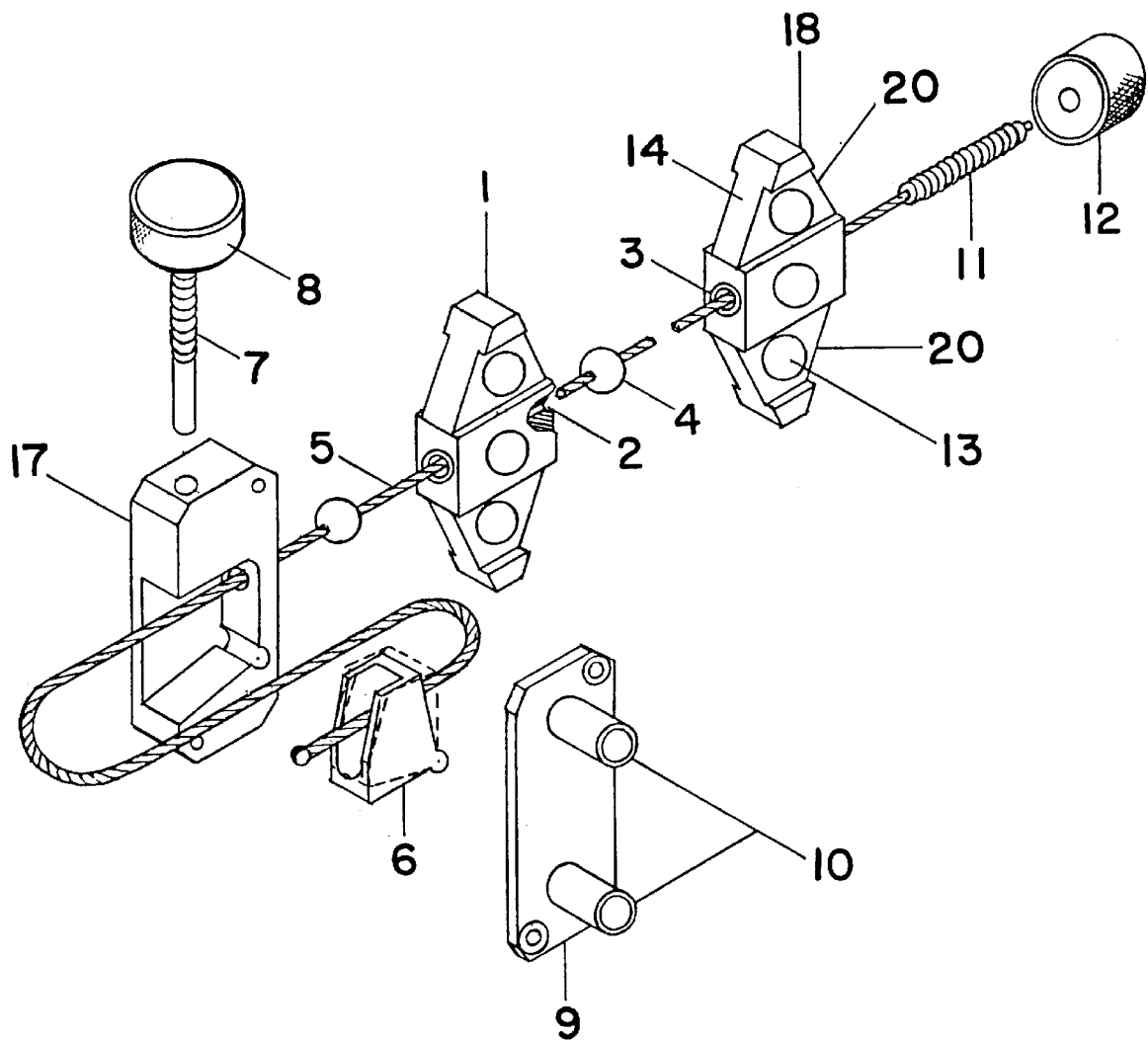
FIG. 2 shows details of the components of the flexible band retractor shown in FIG. 1.
Figure 3:
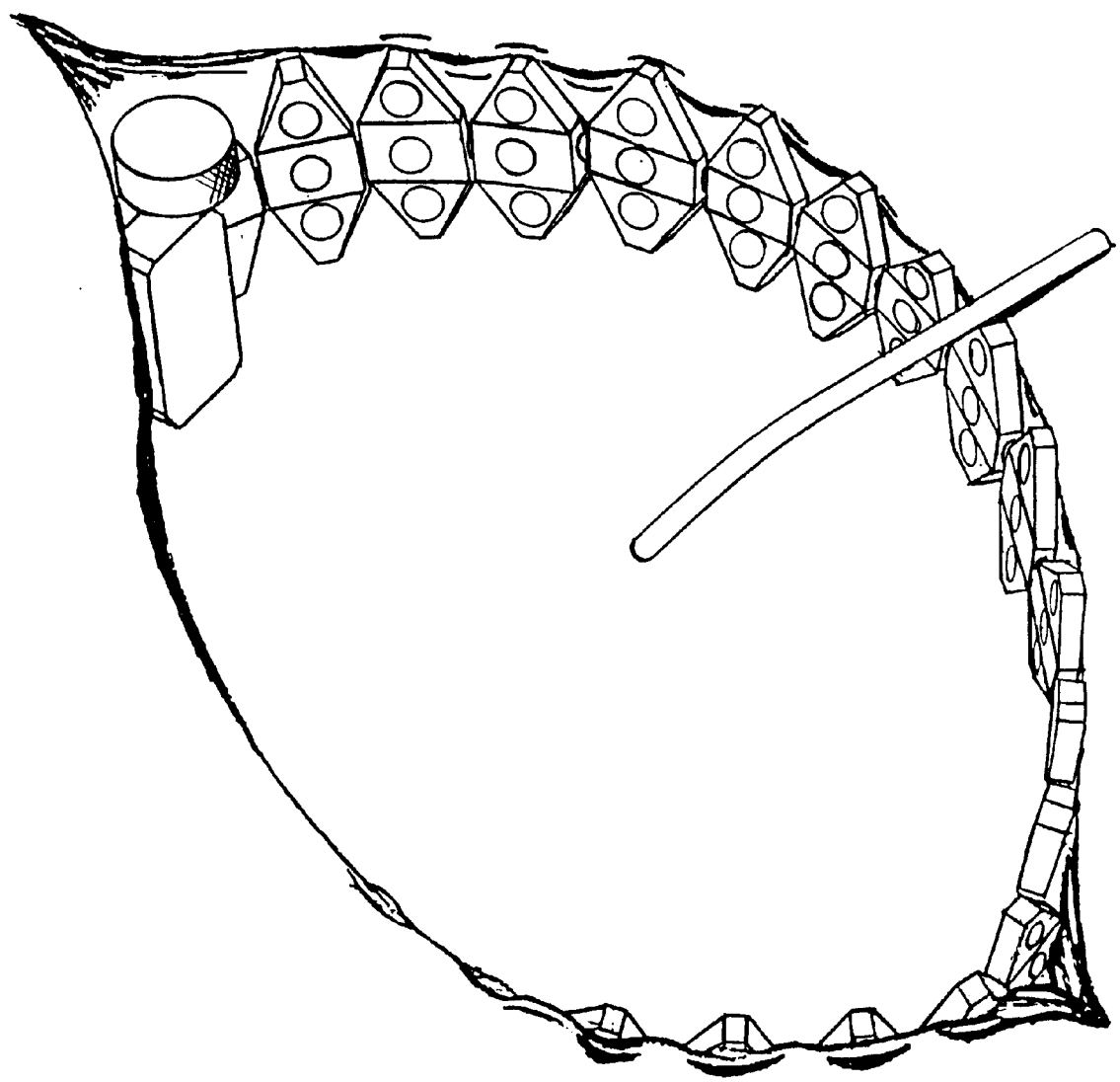
FIG. 3 shows a flexible band retractor inserted entirely into the surgical incision of a total hip arthroplasty.
Figure 4:
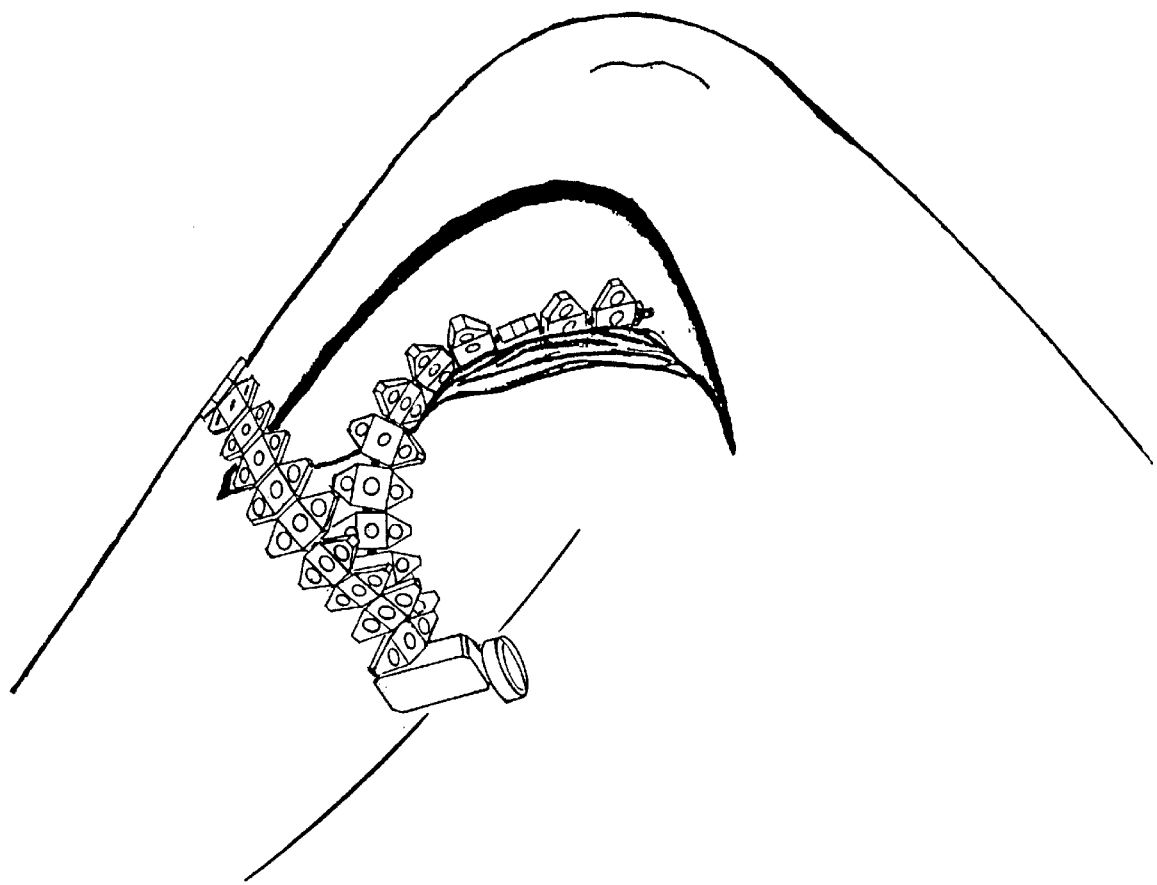
FIG. 4 shows a flexible band retractor partially formed around a lower leg, with a portion running laterally up the leg and thence dipping into the incision of a tibial plateau surgery.

In the embodiment shown in FIGS. 1, 2, 3 and 4, a band consists of a plurality of elements linked together. FIG. 1 shows a band formed into a partial circle. FIG. 2 shows details of this band embodiment. The band has two specialized ends; a tensioner end (#17) and a pre-tensioner end (#18). On the tensioner end is a cover (#9). Anchored to this cover and protruding from it are several cross link pins. Between these two ends are a plurality of elements. The elements (#1) are identical pieces and are shaped and sized such that the assembly thereof is optimized for fitting into incisions for hip surgeries and gripping flesh there-in. The shape also enhances the inter-fitting of accessories and other instruments. The truncated angular sections (#14) allow freedom of angular motion "a", between elements. Additionally, two of these sections side by side form a "V" into which instruments, such as suction tubes and other instruments, can be wedged. Three large holes (#13) are through the faces of the elements. These enhance the gripping of tissue, as do the grooves (#20) across each face. The three holes are also receptacles for the cross link pins (#10), and special accessories. The tensioner end can be linked to any other element by inserting one or more of the cross link pins (#10) protruding from the tensioner cover (#9) into one or more of the three holes (#13) through the faces of the element. There is a transverse hole (#2) through each element. Through this hole (#2) a tensioning cable (#5) passes. At either end of this hole is a spherical section (#3). A spherical ball, (#4) also with a hole through which the tensioning cable (#5) passes, provides alignment and rigidification between the elements. The linking means is the combination of cable (#5), the balls (#4) and the spherical sections (#3) of the elements. The tensioning means is a screw-activated 90 degree angled lever (#6). This angled lever hinges inside the tensioner housing (#17). The knob (#8) drives the screw (#7), forcing the lever to (pull on), tension the cable. To increase rigidity, the tension in the cable is increased, forcing the balls into the sockets of the elements. As the balls are forced into the sockets, the friction between the ball surface and the socket surface increases, resulting in rigidification of the elements to one another. It is this friction that causes the fabric to become stiff This band is flexible in six dimensions. The elements may move in angle a, as discussed above, and in b around the axis of the cable, and in four other axes, which will be designated X, Y, Z and d, following the convention of Cartesian coordinate nomenclature. The band may be very limp, or semi-rigid, or rather rigid, in which state it is stiff enough to hold open a deep incision in a body. The band has a tension release mechanism, the pre-tensioner (#11). This is a "jack screw" that is attached to one end of the cable (#5), opposite that end of the cable that is attached to the tensioning lever (#6). This jack screw has a linear travel sufficient to provide enough slack in the cable so that when required there can be space between the elements and the balls. Turning the pre-tension knob (#12) anti-clockwise releases the pre-tensioner, by releasing the jack screw into the terminal element thereby releasing more of the cable, allowing space between the seats in the elements and the balls. This space affords easy cleaning.

Figure 5:
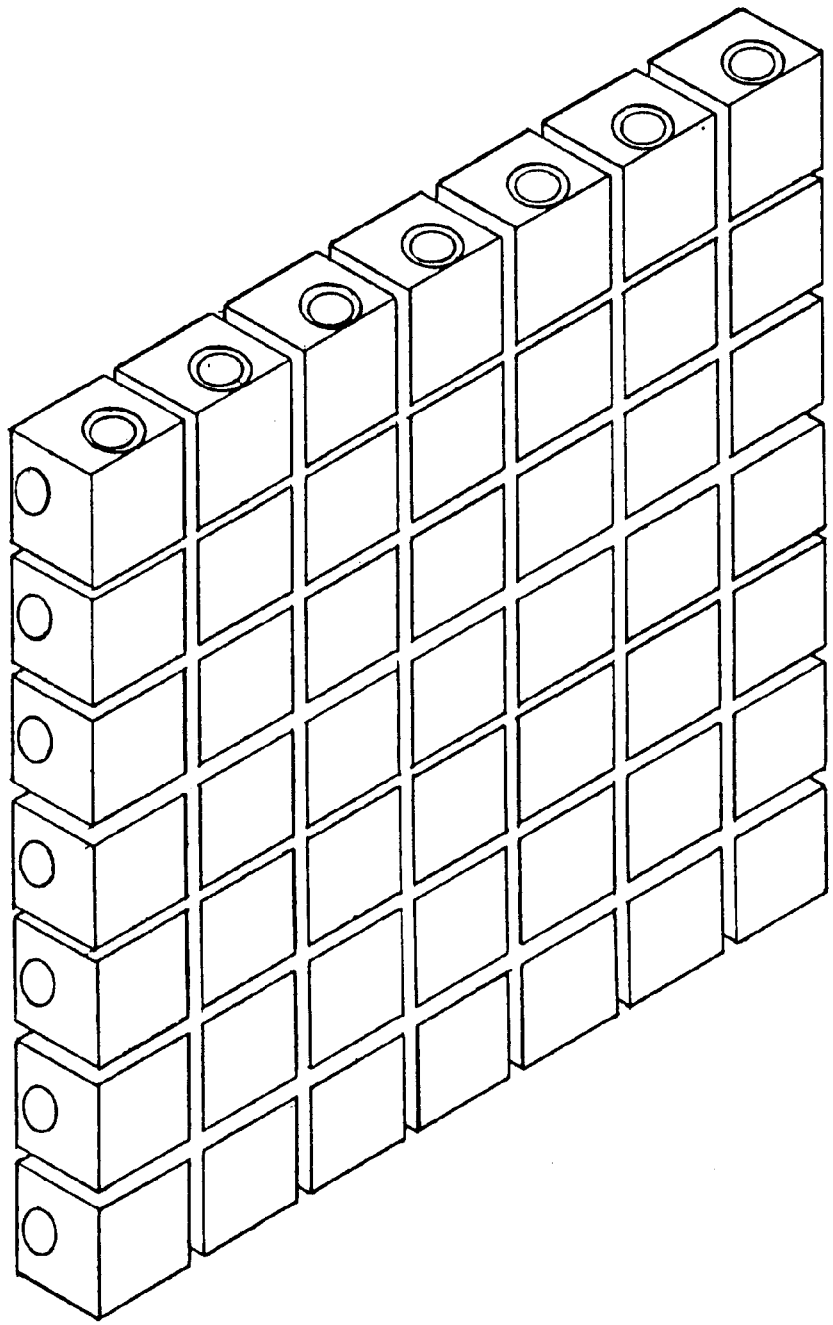
FIG. 5 shows a flexible sheet (tensioners eliminated for clarity).
Figure 6:
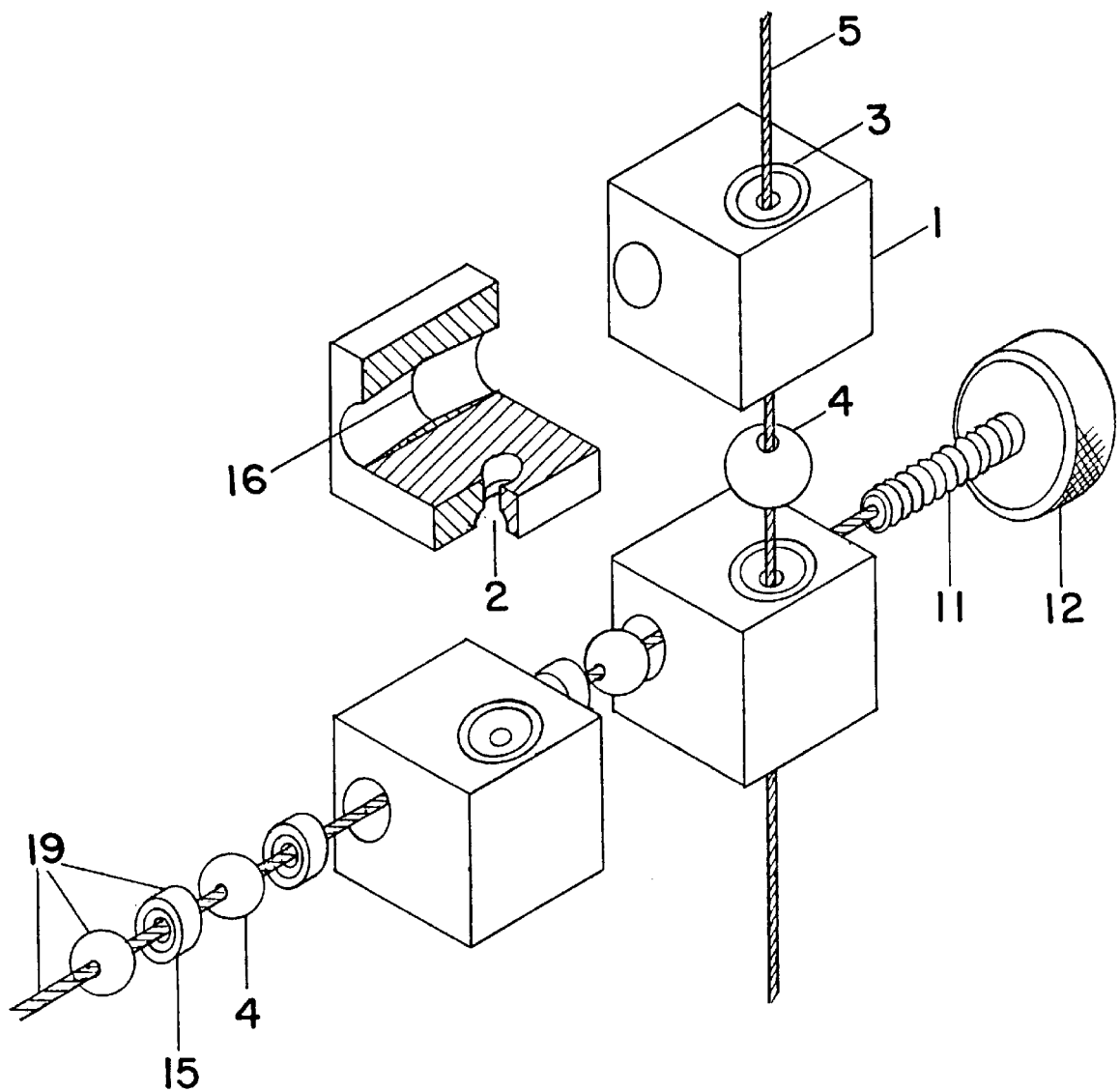
FIG. 6 shows details of the components of a flexible sheet shown in FIG. 5.
Figure 7:
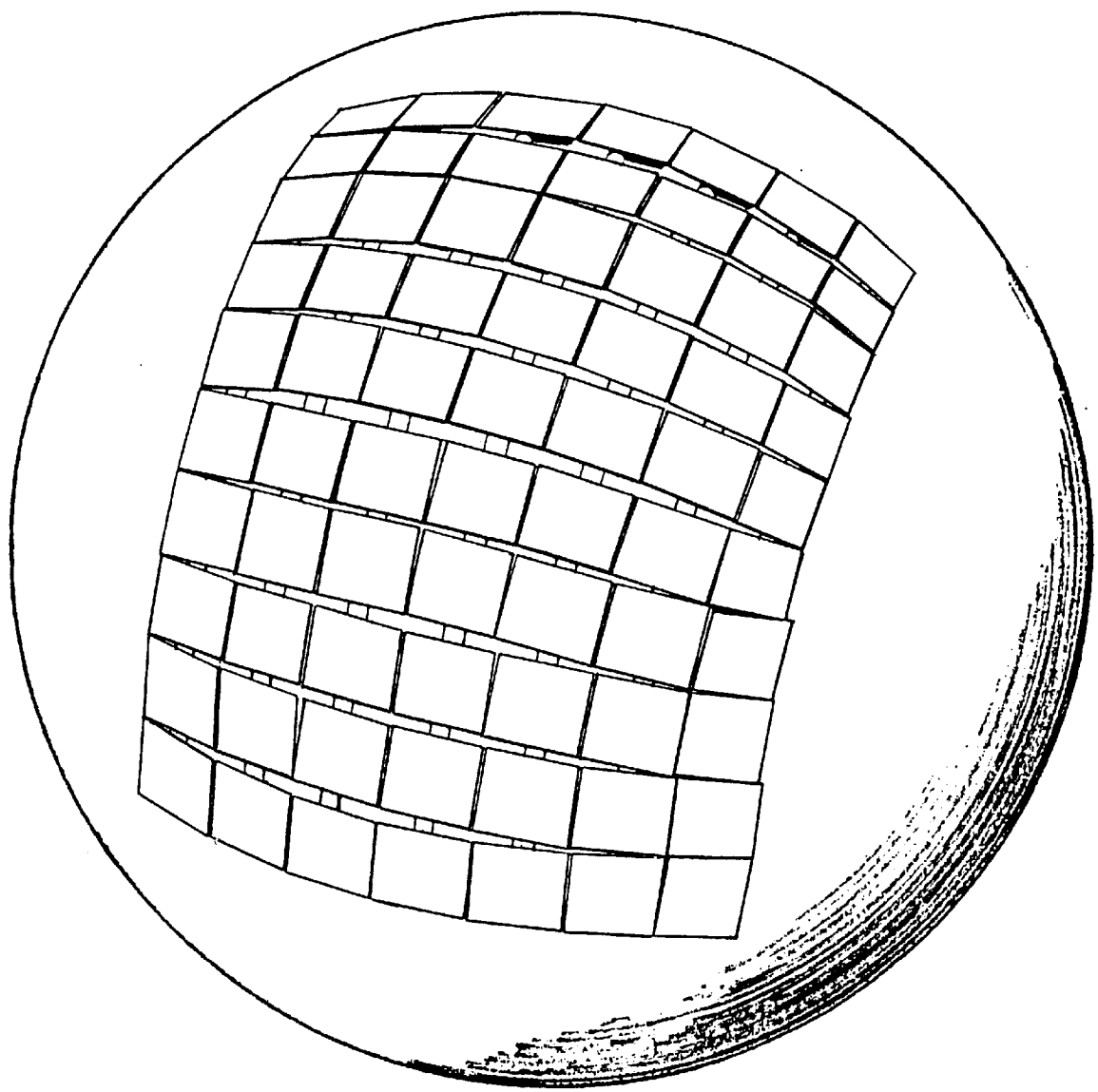
FIG. 7 shows a flexible sheet formed over a section of a sphere (tensioners eliminated for clarity).

In the sheet embodiment, shown in FIGS. 5, 6 and 7, multiple bands are linked together by a second cable system. This second cable system is made up of multiple ball and disk loaded cable matrixes, running at essentially right angles to the tensioning cables (#5) which hold together and rigidify the band elements. FIG. 5 shows seven bands running vertically, side by side up the sheet of paper. For clarity, the cables are not shown in FIG. 5, but the spherical seats are depicted at the ends of the seven bands. (FIG. 6 shows the cables.) Note that each of the bands shown in FIG. 5 has seven elements, and in the side of each of the seven elements of band number one, (numbering from the left side) may be seen a hole (#16) at essentially right angles to the tension cable holes. FIG. 6 shows details of the sheet embodiment. Note that the elements are shown here in cubical shape, but may be shaped differently depending upon the specific use of the sheet. Running vertically are the "bands" which are tensioned by cable (#5) and balls (#4) and spherical seats (#3) as in FIG. 2, and FIG. 6. Connecting these bands all together to create a sheet, is a series of ball and disk loaded cable matrixes (#19) which run essentially at right angles to the bands. The ball (#4) is forced into the spherical seat of the disk (#15), and as in the band, as the tension increases, so the frictional force increases. When tensioned, this ball and disk loaded cable matrix becomes stiff, strong and rod like. These ball and disk loaded cables are shown tensioned by screws, as in the bands, but may be tensioned by any of a number of means. What is unique about the horizontal running cables is that these ball and disk loaded cable matrixes allow the bands to be proximal to one another, or to be separated by varying amounts from to one another. This variable separation is provided by sliding the not tensioned ball and disk loaded cable matrix through a specially designed bi-angled hole (#16). This hole is double angled (relative to the lateral faces of the elements) where the angle is subtended at the central portion length of the hole. When the ball and disk loaded cable matrix is not tensioned it is flexible like a cable and it will slide through the bi-angled hole. However, when the ball and disk loaded cable matrix is tensioned it is stiff; non-compressible, non-extensible and therefore it will not slide through the bi-angled hole. When tensioned, the ball and disc loaded cable matrix locks into the bi-angled hole (#16). Additionally, when the ball and disc loaded cable matrix is tensioned, the resulting rigidification causes the ball and disk loaded cable matrix to become substantially like a solid metal rod. This stiffness results in strength in 4 axes, which combines with the stiffness of the bands, to create a substantially stiff sheet.

From the description above, a number of advantages of my flexible hardware system become evident.

This hardware may be used as a retractor.

As a retractor, this hardware is continuous band or sheet inside the incision, holding open the entire incision.

When used as a totally internal device, this retractor does not protrude above the surgical area unless the surgeon wishes a portion to be up and out of the incision.

As a retractor, this hardware is a continuous band or sheet both inside and outside the incision.

This hardware may be used as a hand formable band, in which case a portion of the band may be utilized outside the incision as an anchor or loop.

This retractor allows hands free surgery; once installed it holds open the entire surgery site until the surgeon wishes to reshape it or remove it.

This retractor does not require external frames, rods, posts, chains, or what have you.

This hardware will serve to hold other instruments, such as a suction tube or a discreet retractor within accessory holes and within notches which are designed into the elements. Because the elements have six degrees of freedom, it is possible to shape the band embodiment in ways and with a finesse unobtainable by any prior instrument, providing highly specific shaping of the tissue.

This hardware may be used as a "curve tracer" in instances where the user wishes to copy a shape from one area and compare it to another area.

This hardware may be used as a fixator, such that it can be formed around or along side an organ, and when shaped and rigidified, act as a "mandrel" to that organ.

This hardware may be used as a mold, providing a 3-dimensional reference.

This hardware does not develop fatigue failure as does solid material when repeatedly bent and straightened.

OPERATION—FIGS. 1, 2, 3 AND 4

In practice, the surgeon employs the flexible band in FIGS. 1 and 2 easily and quickly. The band is pre-tensioned by rotating the pre-tensioner knob (#12), taking up excess cable, and causing intimate contact and some friction force between the balls and the spherical seats in the elements. After making the required incision into the tissue, the surgeon adjusts the flexibility of the band to the desired stiffness by rotating the tensioning knob (#8) and inserts some or all of the band into the incision. In some cases, the surgeon will wish to insert the entire band into the incision, as in some hip procedures. In other cases, the surgeon will find that he can achieve a good result by leaving a portion of the band out of the incision, to serve as an anchor or a collar. In either case, he then forms the band to roughly the suitable shape and required perimeter. If a hoop is desired, the surgeon may then interlock the cross link pins (#10) protruding from the tensioner cover (#9) into holes (#13) in an apposing element anywhere along the length of the retractor, thus establishing an appropriate size loop. Tightening the tensioning knob stiffens the resulting hoop. See FIG. 3, which shows a band inserted totally into an incision. This hoop remains inserted in the surgical site, maintaining the necessary retraction of the tissue. There is no hardware outside the surgical site to get in the way. In the case where the surgeon inserts only a portion of the band into the incision, after the shape is suitable, tightening the knob (#8) stiffens the band so that it will remain where it has been placed. See FIG. 4, which shows a band partially inserted into an incision. Surgery on the leg, including on the tibial plateau, is one case where an external wrap of the band around the leg can act as an anchor to the remaining portion of the stiffened band of which the remaining free end is dipping down into the incision and holding the incision open. To locally further retract tissue in certain spots which require special treatment, the surgeon may select one or more specially shaped devices and snap such devices onto the internal retractor at the appropriate positions. Accessory items may be attached using the holes (#13) in FIG. 2, or the "V" between elements, (See FIG. 3 which shows a suction tube inserted into the "V") or may be hooked over the band. When it is required to change the shape or attitude of this retractor, the surgeon may easily and quickly reduce the stiffness of the hoop assembly by loosening the knob (#8) and then reposition, reshape and re-rigidify the assembly. It will be appreciated that it is easy to adjust the stiffness of the band by very small linear increments, and therefore the shape will never collapse.

OPERATION—FIGS. 5, 6 AND 7

The sheet shown in FIGS. 5 and 7 is used much as the band described above. In essence, the sheet is an assembly of a plurality of bands. In the sheet, the bands are tied together by a ball and disk loaded cable matrix (#19) which allows for variable spacing between each band. Thus, the assembly of bands covers a wider area than a single band. Conceptually, this becomes obvious when one thinks of forming a sheet around a portion of a sphere. To form a sheet around a portion of a sphere, one is actually laying a band along an imaginary "longitudinal" line, (vertical line running up and down the surface of the sphere). Along side this band another band is laid, this also in a vertical direction. The two bands are closer at the "poles" of the sphere than they are at the "equator". See FIG. 7. By repeating this analogy, one soon has a number of bands, alongside each other, but spaced further apart at the equator than at the poles. This is analogous to the longitude lines on a world globe. Because of the requirement that bands have variable spacing, the horizontal cables, (latitude lines) when not tensioned, are designed to slide through the holes (#16) in the bands so that the spacing between the bands can be adjusted. In use, to fill a cavity, or to form a sheet over a spherical section, first tension the bands (longitude) with a nominal tension. Then, lay the sheet into the cavity or over the spherical section, and spread the bands such that they are evenly distributed over the surface. Note again that the spacing between bands will not necessarily be even. When the surface is adequately covered, tension the ball and disk loaded cable matrixes (#19) (latitude). Tensioning the ball and disk loaded cable matrixes rigidities this cable assembly, which in turn locks the spacing between the bands by locking the disk and ball loaded cable matrix in the bi-angular hole (#16) and simultaneously stiffens the sheet in this direction. Lastly, tension the bands to the required final stiffness. When properly tensioned, this sheet is substantially stiff; in fact the sheet is strong enough to retract tissue, and strong enough to retain the shape of the model, even when removed from the model. The sheet can serve as a mold of the model.

CONCLUSION, RAMIFICATIONS, AND SCOPE OF INVENTION

Accordingly, the reader will see that the flexible rod, band and sheet hardware of this invention can be used to hold tissue in surgery. This invention will reduce the number of retractors required. This invention will enhance visibility and accessibility of the object of the surgery, because of its unique size and easy formability. This invention provides highly specific shaping of tissue. This invention will save time and will cut the number of people required to hold retractors. This invention will hold other instruments while retracting tissue. This invention will not fail due to fatigue fracture. This invention will act as a curve tracer. This invention will function as fixator. This invention will act as a mold.

While my above description contains many specifications, these should not be construed as limitations on the scope of the invention, but rather as an exemplification of one preferred embodiment thereof. Many other variations are possible. For example, the ball (#4) may be an integral part of the element on one side, while the other has the seating shown. The cable (#5) may be a rod. The elements may have a different shape, and may be different one to the other. The elements may be articulated. Any variation of the number of elements in both the band and sheet may be employed. The pre-tensioner may be detented with a quick release. A number of different materials may be used. Different sizes may be used. It is reasonable to mold the elements of plastic, or cast of aluminum. The rod or band or the sheet may be encased in other materials. This disclosure describes uses in the field of surgery, but there are many uses in other areas, a few of which are mold making, model making, tooling, fastening and joining, and so on.

Accordingly, the scope of the invention should be determined not by the embodiment(s) illustrated, but by the appended claims and their legal equivalents.

I claim:

1. A surgical retractor, consisting essentially of:

a plurality of substantially planar discrete elements;

means for coupling said elements together so as to form an elongate matrix having first and second ends which has a flexible state in which said elements are moveable relative to one another and a rigid state in which said elements are interlocked into a predetermined rigid configuration, the coupling means providing each of said elements with six degrees of freedom when in the flexible state;

means for attaching said first end to any of said elements in said matrix in a loop configuration, the attaching means including at least one perforation in each of said elements; and wherein said elements can be interlocked in a position which when inserted into a surgical incision retracts internal organs and tissues while allowing fluids to pass through the perforations.

2. The surgical retractor of claim 1, wherein said elements each include a hole positioned transversely to the direction of said at least one perforation, and further wherein said coupling means comprises a plurality of balls linked together by a tension cable which passes through said holes in said elements.

3. The surgical retractor of claim 1, wherein said matrix is of a size and shape adapted to fit completely into, and be self retaining in, the surgical incision.

4. The surgical retractor of claim 3, wherein said attaching means further includes a tensioner housing at said first end of said matrix, said housing having a cover plate with at least one permanently attached pin, said pin being of a size and shape so as to fit into any of said perforations in said elements, thereby facilitating the attachment of said first end to any of said elements so as to form a loop.

5. The surgical retractor of claim 3, wherein each of said elements includes two substantially planar faces, and at least one deep groove on said two planar faces, for enhancing the gripping of tissue by the retractor.

6. Surgical retracting hardware, comprising:

a plurality of discrete elements;

means for cross-linking said elements into a matrix having a sheet configuration, the cross-linking means comprising longitudinal linking means for interlocking said elements into a plurality of longitudinal bands and latitudinal linking means for attaching said longitudinal bands side by side to one another so as to form a sheet, said longitudinal linking means and said latitudinal linking means including means for variable rigidifying said sheet into a unit which is flexible and shapeable by hand when at a low limit of rigidity but substantially strong enough to retain it's shape in three dimensions when at the highest limit of rigidity;

wherein, at said low level of rigidity said longitudinal linking means allows movement of adjacent elements in each of said plurality of longitudinal bands, and said latitudinal linking means provides variable spacing between adjacent longitudinal bands in a direction perpendicular to the elongate axis of said longitudinal bands;

and further wherein, at said highest level of rigidity said longitudinal linking means prevents movement between adjacent elements in each of said plurality of longitudinal bands, and said latitudinal linking means locks said longitudinal bands positionally and angularly in space with respect to one another, such that said sheet may be formed into multiplanar, cylindrical and semi-spherical shapes which are adapted to retract internal organs and tissues during surgery.

7. The surgical retracting hardware of claim 6, wherein each of said elements include a pair of opposing spherical sockets connected to each other by a hole through the element and operatively associated with said longitudinal linking means.

8. The surgical retracting hardware of claim 7, wherein said longitudinal linking means of each longitudinal band comprises a tension cable having thereon a plurality of balls, said tension cable running through the holes in said elements, and said plurality of balls fitting into said spherical sockets when in the rigid state.

9. The surgical retracting hardware of claim 8, wherein each of said elements further includes a bi-angular hole positioned substantially perpendicular to said hole connecting the sockets, and further wherein said latitudinal linking means comprises a ball and disk loaded cable matrix which runs through said bi-angular hole.

* * * * *